(12) United States Patent
Chen

(10) Patent No.: US 8,536,124 B2
(45) Date of Patent: Sep. 17, 2013

(54) ARTIFICIAL DECAPEPTIDE FOR INDUCING VITELLOGENESIS IN FISH

(75) Inventor: Ying-Nan Chen, Pingtung (TW)

(73) Assignee: National Pingtung University of Science & Technology, Pingtung County (TW)

(*) Notice: Subject to any disclaimer, the term of this patent is extended or adjusted under 35 U.S.C. 154(b) by 306 days.

(21) Appl. No.: 13/050,485

(22) Filed: Mar. 17, 2011

(65) Prior Publication Data

US 2011/0226188 A1 Sep. 22, 2011

(30) Foreign Application Priority Data

Mar. 19, 2010 (TW) .............................. 99108197 A

(51) Int. Cl.
*A61K 38/00* (2006.01)
*A61K 38/09* (2006.01)

(52) U.S. Cl.
USPC ........... 514/10.3; 530/313; 530/328; 530/300

(58) Field of Classification Search
None
See application file for complete search history.

(56) References Cited

U.S. PATENT DOCUMENTS

| | | | |
|---|---|---|---|
| 4,443,368 A | 4/1984 | Sherwood et al. | |
| 5,288,705 A | 2/1994 | Zohar | |
| 5,643,877 A | 7/1997 | Zohar et al. | |

FOREIGN PATENT DOCUMENTS

| | | | |
|---|---|---|---|
| GB | 2237571 A | | 5/1991 |
| WO | WO03064460 | * | 8/2003 |

* cited by examiner

*Primary Examiner* — Bridget E Bunner
*Assistant Examiner* — Christina Borgeest
(74) *Attorney, Agent, or Firm* — Muncy, Geissler, Olds & Lowe, PLLC

(57) ABSTRACT

An artificial decapeptide for inducing vitellogenesis in fish, being an analogue of gonadotropin-releasing hormone of chicken is set forth in SEQ ID NO: 2. The artificial decapeptide can be further developed and manufactured into a preparation, which is capable of inducing vitellogenesis in fish. With the implantation of the preparation into body cavity or body wall of bony fish, the induction of vitellogenesis and ovum maturation in bony fish can be successfully achieved.

8 Claims, 4 Drawing Sheets

ARTIFICIAL DECAPEPTIDE FOR INDUCING VITELLOGENESIS IN FISH

BACKGROUND OF THE INVENTION

1. Field of the Invention

The present invention relates to an artificial decapeptide and, more particularly, to an artificial decapeptide for inducing vitellogenesis in fish and its application to aquaculture industry.

2. Description of the Related Art

Marine aquaculture in Taiwan, fish farming in particular, has a long history and been rapid developed in recent decades. Since the advance of aquaculture technique, the fish farming in Taiwan tends to be intensive and industrialized. Accordingly, a significant quantity and quality of broodstock is requested.

The sexual maturation and breeding of fish is involved in a complicated mechanism which has not been well-studied until recent years. Generally, the endocrine system of fish is mainly induced by environmental factors to turn on a hypothalamus-hypophysis-gonad axis responses. In this way, the downstream gonadal developments, including oocyte maturation, vitellogenesis and spawning will be sequentially turned on. Precisely, the hypothalamus will induce the secretion of gonadotropin releasing hormone (GnRH) or gonadotropin inhibiting factor (GnIF), such as dopamine, for catalyzing the synthesis and release of gonadotropin (GtH). The GtH can further phosphorylate protein kinases in ovum or spermatid and induce the steroidogenesis. Finally, the secreted hormone, for example estradiol, leads to vitellogenesis and oocyte maturation, and the ovulation can be sequentially induced by other environmental factors.

In conventional art, GtH, naturally occurred by hypothalamus, are injected into farming broodstock via hypophysation for inducing spawning. However, GtH has big difference among species and have to be genetic expressed rather than chemically synthesized. Hence, the GtH is limited by its higher cost. Otherwise, human chorionic gonadotropin (hCG), commercial LHRHA and domperidome are also used in farming fish. Nevertheless, hCG, commercial LHRHA and domperidome are mainly target to later phase of oocyte development, and which has poor effect on vitellogenesis.

With reference to GB Patent No. 2237571, entitled with "ANALOGUES OF GONADOTROPIN RELEASING HORMONE" GnRH is suggested to play an important in breeding mechanism in vertebrate. Moreover, several naturally occurring vertebrate GnRH has been isolated. However, the conventional invention does not provide a precise application of the GnRH.

Therefore, it is a need of providing an alternative approach for inducing vitellogenesis, ovulation, and spawning of farming fish, in order to improve the conventional technique in aquaculture and establish an effective modulated system for producing high quality and quantity of broodstock.

SUMMARY OF THE INVENTION

The primary objective of this invention is to provide an artificial decapeptide for inducing vitellogenesis in fish, which can promote sexual maturation and vitellogenesis of bony fish.

The secondary objective of this invention is to provide a preparation for inducing vitellogenesis in fish so as to modulate vitellogenesis, ovulation and spawning of farming fish.

Another objective of this invention is to provide a method for inducing vitellogenesis in fish, which can promote the gonadal maturation of broodstock and the production of fish farming.

An artificial decapeptide for inducing vitellogenesis in fish, being an analogue of gonadotropin-releasing hormone of chicken, which is set forth in SEQ ID NO: 2.

A preparation for inducing vitellogenesis in fish comprises an artificial decapeptide described above.

A method for inducing vitellogenesis in fish, implants a preparation described above into body cavity or body wall of bony fish for inducing vitellogenesis and ovum maturation.

Further scope of the applicability of the present invention will become apparent from the detailed description given hereinafter. However, it should be understood that the detailed description and specific examples, while indicating preferable embodiments of the invention, are given by way of illustration only, since various others will become apparent from this detailed description to those skilled in the art.

BRIEF DESCRIPTION OF THE DRAWINGS

The present invention will become more fully understood from the detailed description given herein below and the accompanying drawings which are given by way of illustration only, and thus are not limitative of the present invention, and wherein.

Figure 1:
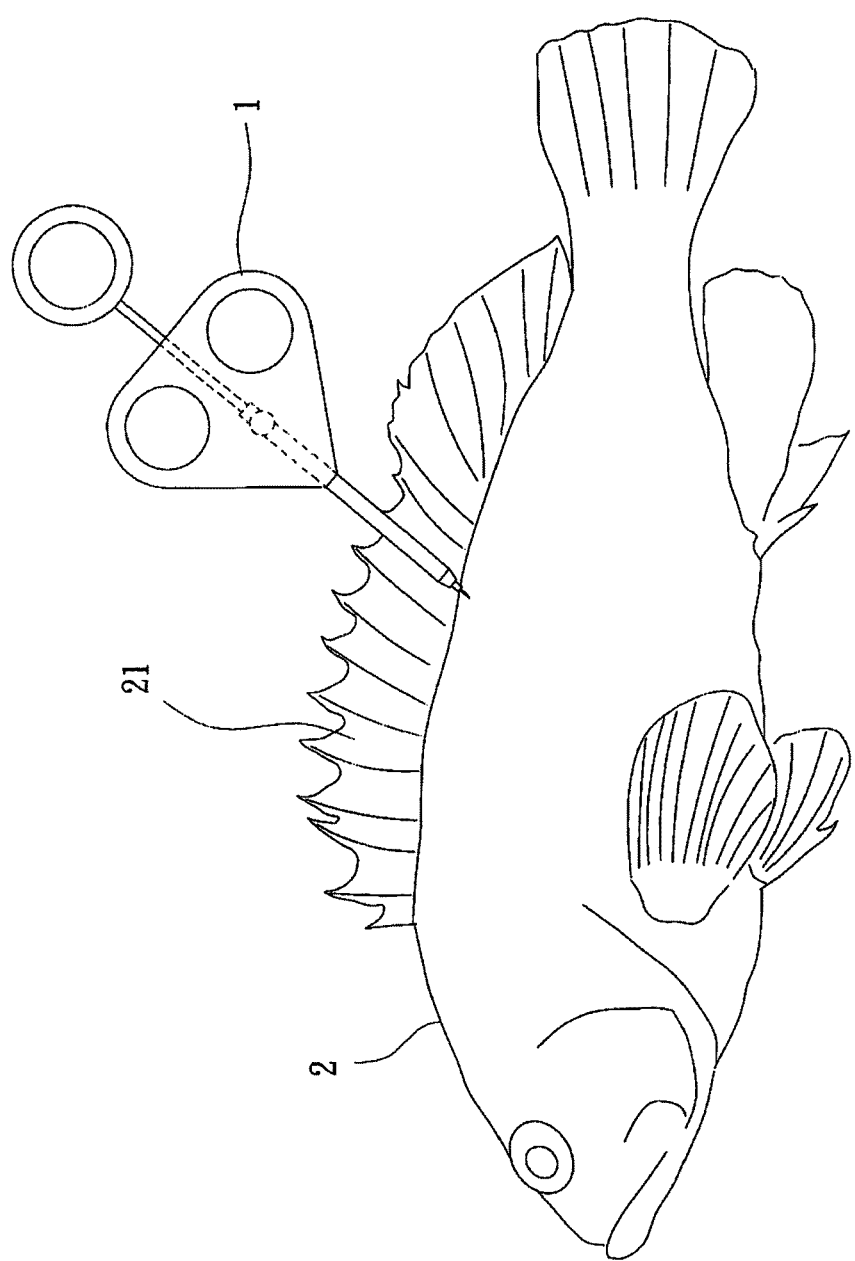
FIG. 1 is a diagram illustrating implantation of decapeptide of the present invention.

All figures are drawn for ease of explaining the basic teachings of the present invention only; the extensions of the figures with respect to number, position, relationship, and dimensions of the parts to form the preferred embodiment will be explained or will be within the skill of the art after the following teachings of the present invention have been read and understood. Further, the exact dimensions and dimensional proportions conforming to specific force, weight, strength, and similar requirements will likewise be within the skill of the art after the following teachings of the present invention have been read and understood.

DETAILED DESCRIPTION OF THE INVENTION

The present invention provides an artificial decapeptide for inducing vitellogenesis in fish according to naturally occurring gonadotropin releasing hormone II (GnRH-II) of birds, such as chicken, duck, and goose. The artificial decapeptide can induce vitellogenesis in fish. With implantation of the artificial decapeptide into body cavity or body wall of bony fish, the sexual maturation, as well as ovulation and spawning of bony fish can be successfully induced so as to modulate the breeding season of female fish.

Precisely, the artificial decapeptide of the present invention is designed based on naturally occurring chicken GnRH-II as set forth in SEQ ID NO: 1, by artificially synthesizing the decapeptide via a solid-phase peptide synthesis method. The artificial decapeptide of the present invention comprises ten amino acids and is recorded in SEQ ID NO: 2. In comparison with the naturally occurring chicken GnRH-II, the glutamic acid (Glu) of the artificial decapeptide in N-terminal domain does not cyclized to form pyro-Glu, and the glycine (Gly) in C-terminal domain does not lactamize to form Gly-NH$_2$. Accordingly, all of the ten amino acids of the artificial decapeptide in the present invention are naive and unblock, which only share minor structural differences between the natural occurring chicken GnRH-II. With such differences, the artificial decapeptide of the present invention is capable of being sequenced by Edman degradation. Due to the species similarity of the naturally occurring GnRH, the artificial decapeptide of the present invention can induce hypophysis-gonal axis responses, turn on endocrinal system, and activate vitellogenesis of fish.

Therefore, with the artificially decapeptide of the present invention, it is sufficient to develop a preparation for inducing vitellogenesis in fish. The preparation of the present invention comprises the above artificial decapeptide, with a preferable dose of 10 µg to 5 mg for per kg of designated target. Generally, a fundamental adjustment in the dose of the artificial decapeptide is allowable in accordance with body weight or species of the designated target, for example, 100 µg to 500 µg for per kg of sea bass.

In the preferable embodiment, the decapeptide of the present invention is mixed with a substrate, and further stuffed and manufactured in a glass tube, for pressing and solidifying the artificial decapeptide of the present invention. Under the procedures above, the preparation of the present invention can be encapsulated with the substrate, and becomes the form of a sustained-release capsule. Precisely, the substrate comprises cholesterol, cellulose and little oil, with the cholesterol at a total mass proportion of 50% to 95%, with the cellulose at a total mass proportion of 5% to 50%, and with the oil being vegetable oil or coconut oil. The oil makes the artificial decapeptide more adhesive so as to be easier in pressing. With such arrangement, the cellulose provides tissues-supporting function for maintaining the structure of the preparation so that the artificial decapeptide of the present invention can be entirely covered with the cholesterol and capable of being sustaining released. Furthermore, since the cholesterol is an important material in hormone-synthesis, the cholesterol of the preparation can be also useful for synthesizing gonadotrophin in bony fish. In this way, the artificial decapeptide can be persistently released and induce the sexual maturation of bony fish.

Additionally, a method for inducing vitellogenesis in fish can also be developed, by implanting the preparation of the present invention into body cavity or body wall of bony fish, for example in lateral muscle or abdomen cavity, in order to inducing the sexual maturation and vitellogenesis in the bony fish. With reference to FIG. 1, the preparation of the present invention is preferably implanted into lateral muscle adjacent to dorsal fin 21 of a bony fish 2 by an injector 1 in the present embodiment. Accordingly, the decapeptide in the preparation can be sustaining released into the bony fish for long-term inducing the hypophysis to synthesize and secrete gonadotropin (GtH) so that the vitellogenesis and breeding of the bony fish can be achieved.

For further proving the functions of the decapeptide in the present invention, the preparation of the present invention is implanted into a farming bony fish, and the vitellogenesis of the bony fish is monitored and recorded in the following paragraphs.

Figure 2A:
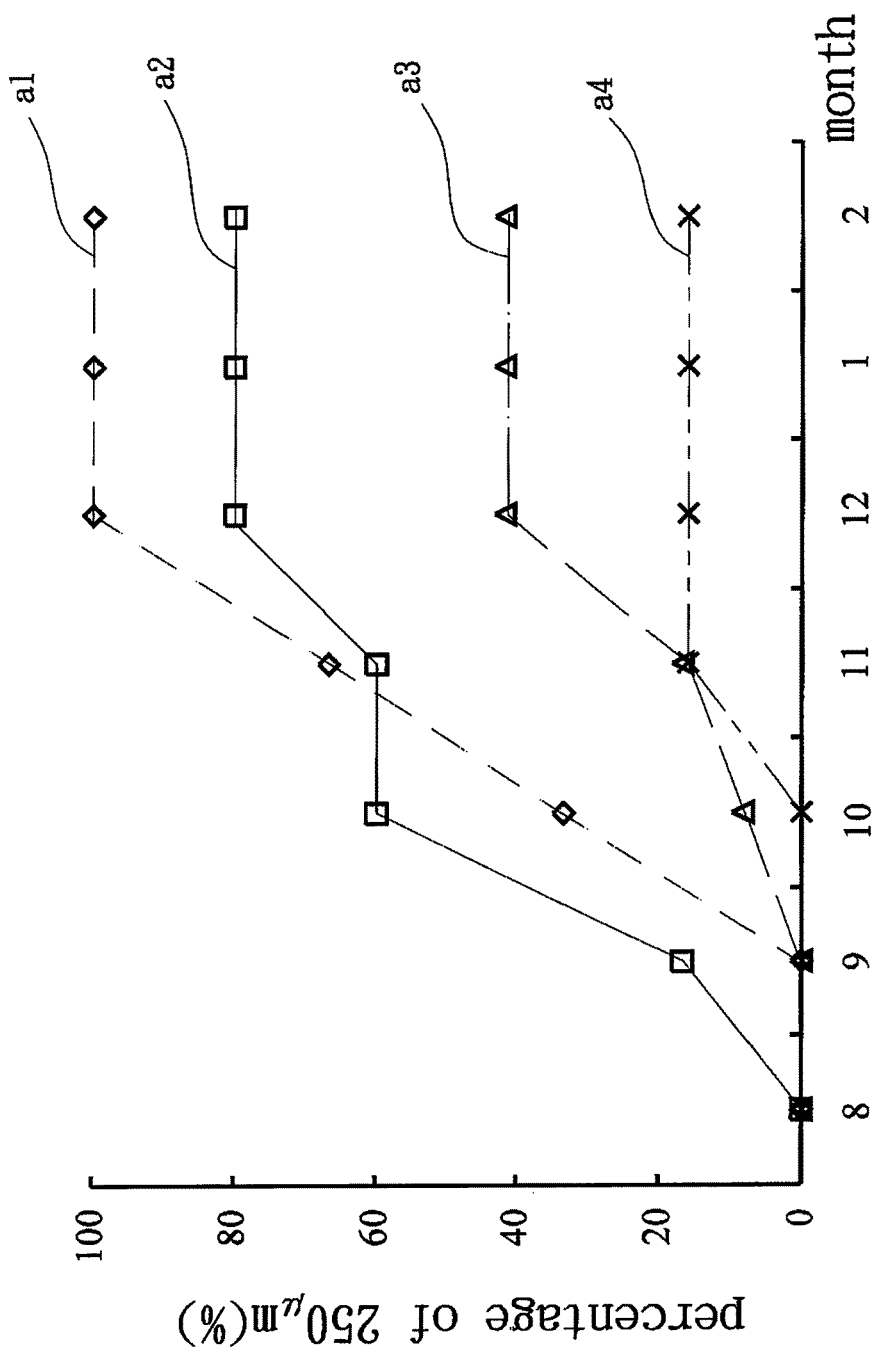
FIG. 2a is a line chart illustrating responses of *Epinephelus coioides* on decapeptide-induction of the present invention.
Figure 2B:
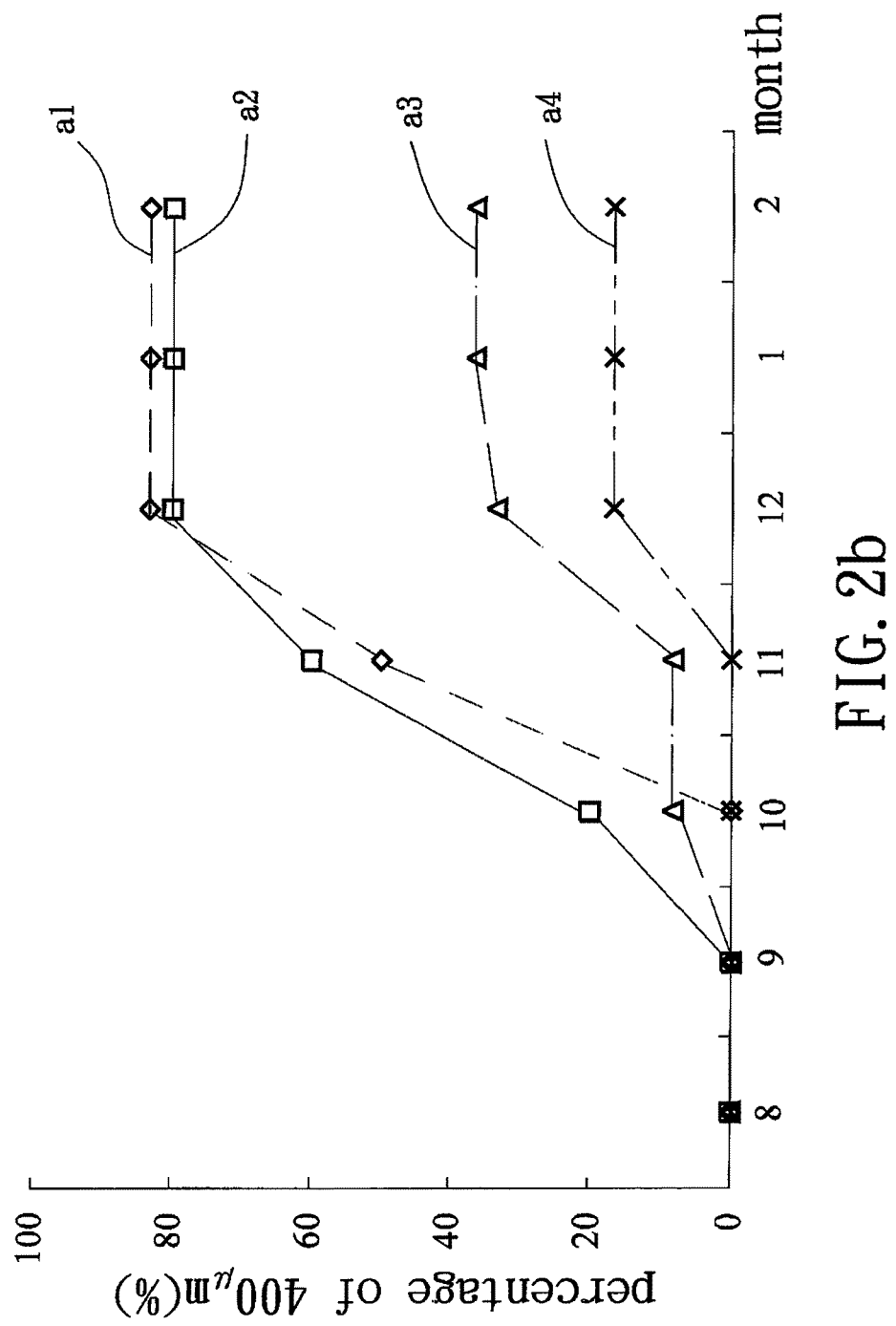
FIG. 2b is another line chart illustrating responses of *Epinephelus coioides* on decapeptide-induction of the present invention.

Referring to FIGS. 2a and 2b, the responses of *Epinephelus coioides* on decapeptide-induction are shown. In the present embodiment, several farming *E. coioides*, around 2 to 3.5 kg in weight, are prepared and randomly assigned into four groups including (a1), (a2), (a3) commercial reagent group and (a4) control group. With reference to TABLE 1 below, the four groups of *E. coioides* are separately treated of the preparation of the present invention, a commercial hormone reagent LHRHA (Sigma-Aldrich, MO, USA) and cholesterol. In the present embodiment, all of the preparation, the commercial hormone reagent LHRHA and the cholesterol are manufactured into the form of a sustained-release capsule, and respectively implanted into *E. coioides* accordingly to the method described above. Moreover, ova of each group of *E. coioides* are collected and analyzed monthly after implantation for monitoring the vitellogenesis in each group of *E. coioides*. The ovum maturation of each group of *E. coioides* is determined in accordance with the size and accumulation of the ovum. Generally, the oocyte diameter is approximately at 10 µm to 70 µm in stage of ovarian follicle, at 70 µm to 120 µm in the first stage of oocyte development, at 120 µm to 150 µm in the second stage of oocyte development, and more than 400 µm in the third stage of oocyte development, also known as maturated stage.

TABLE 1

| group assignments of *Epinephelus coioides* | | |
|---|---|---|
| Groups | Implant | Dose (µg) |
| (a1) | preparation | 100 |
| (a2) | preparation | 200 |
| (a3) | LHRHA | 100 |
| (a4) | cholesterol | 100 |

In FIGS. 2a and 2b, it is noted that the *E. coioides* with the preparation treatment show significant ovum maturation after implantation, with 80% to 100% of *E. coioides* achieving more than 250 µm of oocyte diameter in four months (see FIG. 2a, curves a1 and a2). Moreover, around 80% to 83.3 of *E. coioides* mature and have more than 400 µm of oocyte diameter (see FIG. 2b, curves a1 and a2). On the other hand, the *E. coioides* with LHRHA treatment and cholesterol treatment show poor ovum maturation after implantation, with only 36.4% and 16.7% of the *E. coioides* respectively being mature and achieving 400 µm of oocyte diameter in four months (see curves a3 and a4).

Additionally, in FIG. 2b, the *E. coioides* in groups (a1) and (a2) have the preparation treatment in August, and then show ovum maturation in December. Hence the ovulation of the *E. coioides* in the groups (a1) and (a2) can be inducible and achieved by providing a catalyst, such as GtH or mature male broodstock. It is suggested that the preparation of the present invention not only can effectively induce the sexual maturation of the *E. coioides*, but also can modulate the ovulation and spawning of the *E. coioides*. As a result, the breeding season of the *E. coioides* can be shifted from general spring-summer to autumn-winter. Furthermore, it is proved that the preparation of the present invention is more efficient than other commercial hormone reagents in gonadal induction of bony fish. Therefore, with the decapeptide, as well as the preparation of the present invention, the vitellogenesis, ovulation and spawning of the bony fish can be successfully induced and monitored.

Figure 3:
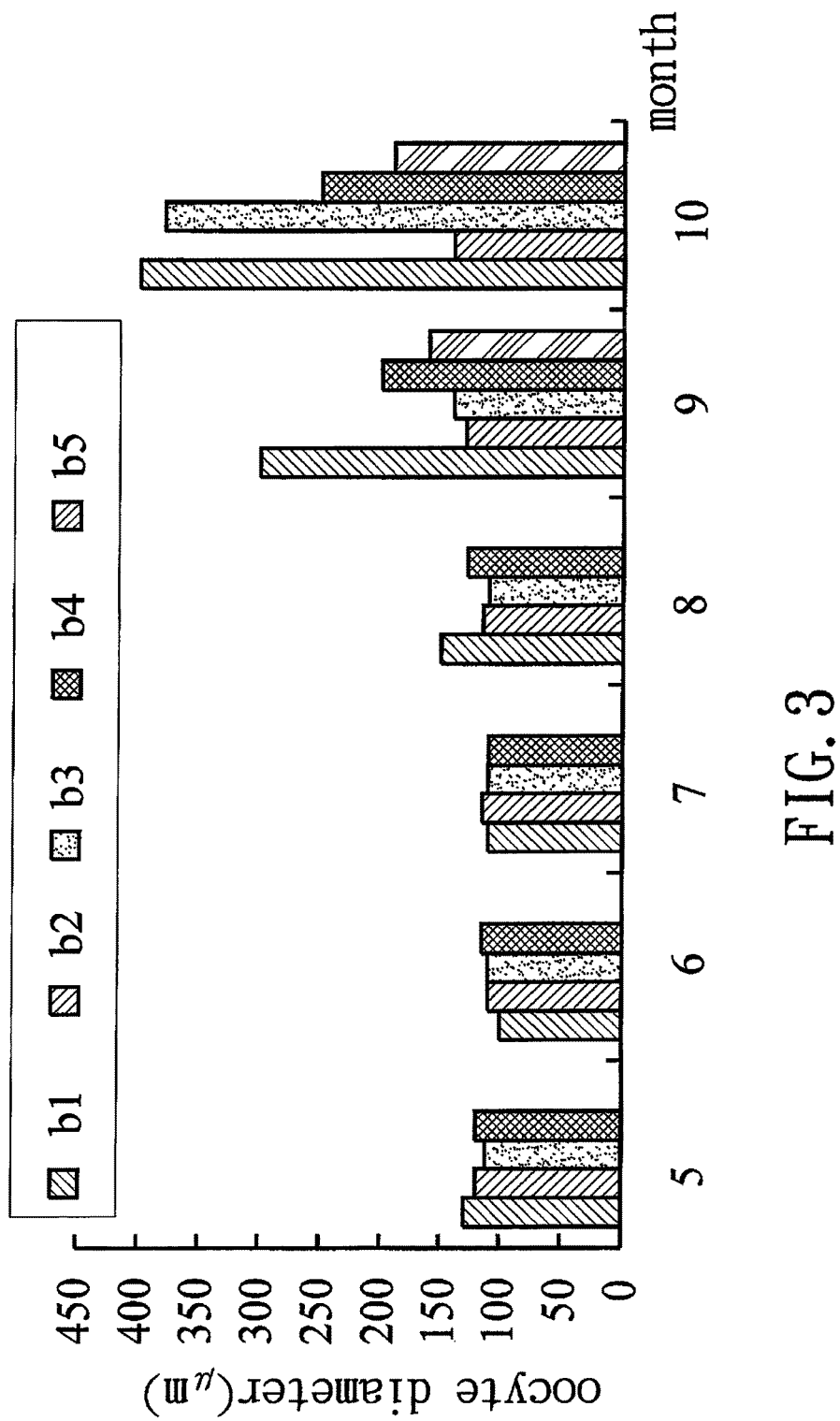
FIG. 3 is a bar chart illustrating responses of *Mugil cephalus* on decapeptide-induction of the present invention.

Referring to FIG. 3, the responses of *Mugil cephalus* on decapeptide-induction are shown. In the present embodiment, several farming *M. cephalus*, are prepared and randomly assigned into five groups including (b1), (b2) ovaprin group, (b3) estradiol group, (b4) MixT group and (b5) control group. With reference to TABLE 2, the five groups of *M. cephalus* are separately treated of the preparation of the present invention, various commercial hormone reagent including ovaprin, estradiol and MixT (Sigma-Aldrich, MO, USA), and blank. The ovaprin comprises domperidone and naturally occurring salmon GnRHa, the MixT comprises androgen mixture. In the present embodiment, the preparation and all of the commercial hormone reagents are manufactured into the form of a sustained-release capsule, and respectively implanted into each group of *M. cephalus* accordingly to the method described above. Moreover, ova of each group of *M. cephalus* are collected and analyzed monthly after implantation for monitoring the vitellogenesis in each group of *M. cephalus*. The ovum maturation of each group of *M. cephalus* is also determined in accordance with the size and accumulation of the ovum.

TABLE 2 group assignments of *Mugil cephalus*

| Groups | Implant | Dose |
|--------|---------|------|
| (b1) | preparation | 400 μg |
| (b2) | ovaprin | 400 μl |
| (b3) | estradiol | 1000 μg |
| (b4) | MixT | 1000 μg |
| (b5) | — | — |

In FIG. 3, it is noted that the *M. cephalus* with the preparation treatment in May show significant ovum maturation in three months after implantation, with oocyte diameter developing to more than 400 μm in October (see bar b1). In contrast, *M. cephalus* in other groups show slowly and slightly ovum developments till October, only with the *M. cephalus* in the group b3 have about 380 μm of oocyte diameter (see bars b2 to b5).

Through the present invention, the artificial decapeptide for inducing vitellogenesis in fish is provided based on naturally occurring chicken GnRH-II. The artificial decapeptide can effectively induce hypophysis-gonal axia responses in bony fish and activates the vitellogenesis of the bony fish. With the artificial decapeptide of the present invention, the preparation and an alternative approach for inducing vitellogenesis in fish can also be provided, in order to modulate the vitellogenesis, ovulation and spawning of bony fish. By implanting the preparation into the bony fish, the sexual maturation of the female bony fish can be easily achieved so as to facilitate the female fish breeding.

The present invention is sufficient to be further applied to aquaculture industry, by establish a modulated system of broodstock breeding with the artificial decapeptide, the preparation and method of the present. In this way, the vitellogenesis, ovulation, and spawning of farming fish can be successfully controlled so that an excellent quantity and quality of broodstock can be easily obtained. Accordingly, the farming technique in aquaculture industry will be dramatically improved.

Thus, since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

```
                      SEQUENCE LISTING

<160> NUMBER OF SEQ ID NOS: 2

<210> SEQ ID NO 1
<211> LENGTH: 10
<212> TYPE: PRT
<213> ORGANISM: Gallus gallus

<400> SEQUENCE: 1

Glu His Trp Ser His Gly Trp Thr Pro Gly
1               5                   10

<210> SEQ ID NO 2
<211> LENGTH: 10
<212> TYPE: PRT
<213> ORGANISM: Artificial Sequence
<220> FEATURE:
<223> OTHER INFORMATION: with unblock N-terminal and C-terminal and is
      artificially synthesized by solid-phase peptide synthesis based on
      naturally occurring

<400> SEQUENCE: 2

Glu His Trp Ser His Gly Trp Thr Pro Gly
1               5                   10
```

It is indicated that the preparation of the present invention is more effective in gonadal induction than other commercial reagents, and which shows efficient effects both in vitellogenesis and sexual maturation of the *M. cephalus*. Therefore, with the preparation of the present invention, as well as the artificial decapeptide of the present invention, the vitellogenesis, ovulation and breeding of the bony fish can be successfully induced and monitored.

What is claimed is:

1. An artificial decapeptide for inducing vitellogenesis in fish, wherein said artificial decapeptide is an analogue of chicken gonadotropin-releasing hormone, wherein said analogue comprises the sequence set forth in SEQ ID NO: 2.

2. A preparation for inducing vitellogenesis in fish, comprising an artificial decapeptide as defined in claim 1.

3. The preparation for inducing vitellogenesis in fish as defined in claim 2, wherein the artificial decapeptide is encapsulated in a substrate comprising cellulose, cholesterol, and oil.

4. The preparation for inducing vitellogenesis in fish as defined in claim 2, wherein the artificial decapeptide is administered at a dose of 10 μg to 5 mg per kg of body weight.

5. The preparation for inducing vitellogenesis in fish as defined in claim 2, wherein the preparation is in the form of a sustained-release capsule.

6. A method for inducing vitellogenesis in fish comprising administration of a preparation as defined in claim 2 into the body cavity or body wall of a bony fish, wherein said administration induces vitellogenesis and ovum maturation.

7. The method for inducing vitellogenesis in fish as defined in claim 6, wherein said body cavity or body wall of the bony fish is the lateral muscle.

8. The method for inducing vitellogenesis in fish as defined in claim 6, wherein said body cavity or body wall of the bony fish is the abdominal cavity.

* * * * *